United States Patent
Nathan

Patent Number: 6,058,735
Date of Patent: May 9, 2000

[54] PRINTED COLD PACK

[76] Inventor: William F. Nathan, N9564 Big Spring Dr., Whitewater, Wis. 53190-3917

[21] Appl. No.: 09/073,091

[22] Filed: May 5, 1998

[51] Int. Cl.[7] .................................................. F25B 3/08
[52] U.S. Cl. .......................................... 62/530; 62/457.2
[58] Field of Search ....................... 62/530, 429, 457.2, 62/529

[56] References Cited

U.S. PATENT DOCUMENTS

| | | |
|---|---|---|
| D. 361,476 | 8/1995 | Bidwell . |
| 2,709,905 | 6/1955 | Dunlap . |
| 2,939,299 | 6/1960 | Sherbloom ............................ 249/111 |
| 3,095,291 | 6/1963 | Robbins ....................................... 62/4 |
| 3,220,684 | 11/1965 | Milne . |
| 3,545,230 | 12/1970 | Morse ....................................... 62/530 |
| 3,638,784 | 2/1972 | Bodolay et al. . |
| 3,808,084 | 4/1974 | Doty . |
| 4,174,598 | 11/1979 | Shepherd et al. ........................ 53/431 |
| 4,325,230 | 4/1982 | Driscoll et al. . |
| 4,404,820 | 9/1983 | Romaine . |
| 5,150,815 | 9/1992 | Saklad . |
| 5,190,033 | 3/1993 | Johnson ................................. 607/108 |
| 5,273,182 | 12/1993 | Laybourne . |
| 5,603,219 | 2/1997 | Kolb . |
| 5,887,437 | 3/1999 | Maxim ......................................... 62/4 |

*Primary Examiner*—Henry Bennett
*Assistant Examiner*—Melvin Jones
*Attorney, Agent, or Firm*—Meroni & Meroni Professional Corporation; Charles F. Meroni, Jr.

[57] ABSTRACT

This invention concerns a multifunctional cold pack comprising: a plurality of nonpermeable, flexible heat-sealable film layers each having a perimeter and being located in a first plane. The plurality of nonpermeable, flexible heat-sealable film layers are heat sealed together at the perimeters to form an interior cavity concentrically enclosed thereby and the interior cavity is geometrically contoured to coexist between the first plane and a second plane located parallel to the first plane. The plurality of nonpermeable, flexible heat-sealable film layers are constructed of a transparent material. A clear gelatinous material is encapsulated without substantial air contamination within the interior cavity and has temperature regulation, flexibility, and load-bearing properties. At least one insert is moldably movable and semi-rigidly placed in the clear gelatinous material and is sized, shaped, and dimensioned to be interposed between the plurality of nonpermeable, flexible heat-sealable film layers. The multifunctional cold pack thereby allows each insert to be viewed through the plurality of nonpermeable, flexible heat-sealable film layers and the clear gelatinous material and imparts optical effects when each insert is so viewed. The multifunctional cold pack has a pleasant tactual texture when applying external pressure force to touch the plurality of nonpermeable, flexible heat-sealable film layers or to flex the multifunctional cold pack. The multifunctional cold pack is elastic and aesthetically appealing and thereby provides means for cooling, supporting, medicinal, advertising, entertaining, and shipping.

A method of making a printed cold pack is also provided and comprises the steps of: laying a coiled first film layer onto a support device; forming the laid first film layer to create a cavity; partially filling the cavity of the formed first film layer with a gelatinous material; chilling the gelatinous material in the partially filled cavity; placing a printed insert in the partially filled cavity; chilling the gelatinous material supporting the placed printed insert in the partially filled cavity; completely filling the partially filled cavity with the gelatinous material to encapsulate the placed printed insert; chilling the gelatinous material encapsulating the placed printed insert in the completely filled cavity; laying a coiled second film layer over the completely filled cavity; sealing the laid second film layer to the laid first film layer to sealingly enclose the gelatinous material and placed printed insert to form a printed cold pack; moving the support device aside and conveying the formed printed cold pack; cutting the sealed second film layer and the sealed first film layer on the conveyed printed cold pack; and ejecting the cut printed cold pack to a packaging device and collecting the scrap film layer.

19 Claims, 4 Drawing Sheets

PRINTED COLD PACK

BACKGROUND OF THE INVENTION

1. Field of the Invention

The present invention relates to a cold pack for multi-functional uses. More specifically, my invention is a printed cold pack that is primarily intended for use with advertising, cooling, aesthetic, medicinal, shipping, and entertainment uses.

2. Description of the Prior Art

In the art of cold packs a cold pack or cold compress is used for applying a cooling means to a portion of a human or animal body or to an item of commerce. The cold pack contains chemicals sealingly enclosed within a package that can itself be deformed to conform to the shape of whatever the cold pack is applied against.

The state of the art is such that cold compresses have been developed to solve varying problems by means of differing chemical and physical structures of the cold compress. For example, in U.S. Pat. No. 4,404,820 a Cold Compress comprising a tough flexible envelope which sealingly encloses a thin gel-like pad that incorporates a coagulated gel is disclosed. This compress claims to remain in a soft and pliable but solid condition at all times and between varying temperatures.

What has not been disclosed in the prior art is a cold compress that utilizes an inserted printed insert for use with advertising, cooling, medicinal, aesthetic, shipping, and entertainment purposes. Though products exist which place printing and designs on the outer package itself, no product has been disclosed that combines an internally inserted printed insert or design image with a cold compress to hence create a multifunctional cold pack.

In U.S. Pat. No. 5,603,219 an Ice Cell For The Cooling Of Drinks is disclosed. This device comprises a closed hollow body filled with a freezable liquid, such as distilled water. The closed hollow body is made partially of a transparent material and has at least one insert which is freely movable within and which is inserted by rolling the insert up and inserting it through a small opening in the synthetically made hollow body.

What is needed then is a cold pack or cold compress that provides a means for advertising, cooling, shipping, entertaining, and aesthetically appealing a user.

Accordingly, it is a principal object of my invention to provide a printed cold pack for advertising, cooling, aesthetically appealing, shipping, and entertaining.

It is a further object of my invention to provide a method of manufacturing the printed cold pack so as to insert any printed insert or object within the printed cold pack.

It is a still further object of my invention to provide the ability to insert any two dimensional or three dimensional object within the printed cold pack.

It is a further object of my invention to provide a printed cold pack that is flexible, nonpermeable, and is capable of retaining a temperature for a period of time.

It is a still further object of my invention to provide a printed cold pack that imparts optically aesthetic images for all of the purposes heretofore stated while being enabled to create a pleasantly palpable sensation for the user who applies an external pressure force to the printed cold pack.

Other objects of my invention, as well as particular features, elements, and advantages thereof, will be elucidated in, or apparent from, the following description and the accompanying drawing figures.

SUMMARY OF THE INVENTION

According to my present invention I have provided a printed cold pack for advertising, cooling, medicinal, aesthetic, shipping, or entertainment purposes comprising: a transparent formed film layer having a first perimeter edge, being capable of flexing, and forming a cavity, the transparent formed film layer being constructed of a nonpermeable, formable heat-sealable material, the first perimeter edge being located in a first plane and concentrically enclosing the cavity, the cavity having a contour and a geometrical edge, and being shaped in a second plane, the second plane being positioned in parallel, offset, and superimposed relation to the first plane, the transparent formed film layer having a tactual formed film layer texture, a formed film layer shape, and a formed film layer size; a clear gelatinous material placed within and substantially filling the cavity, the clear gelatinous material being free flowing and having temperature retaining and load-bearing properties and being capable of flexing and elastically responding to an external pressure force; a transparent nonformed film layer having a second perimeter edge being sealingly connected to the first perimeter edge to thereby sealingly enclose the clear gelatinous material without substantial air contamination, the transparent nonformed film layer being capable of flexing, the transparent nonformed film layer being constructed of nonpermeable, formable heat-sealable material, the second perimeter edge being located in the first plane and being substantially parallel to the first perimeter edge, the transparent nonformed film layer having a tactual nonformed film layer texture, a nonformed film layer shape, and a nonformed film layer size; and at least one printed insert having an insert size, an insert shape, and an insert dimension, each printed insert being incrementally encapsulated and sandwiched within the clear gelatinous material and being sized and configured to be interposed between the transparent formed film layer and the transparent nonformed film layer, the printed insert being oriented in the clear gelatinous material so as to be externally viewed through either the transparent formed film layer or the transparent nonformed film layer and to impart optically aesthetic images when so viewed, the clear gelatinous material being shaped readily by the external pressure force, the printed insert being capable of induced moldable movement as the clear gelatinous material is shaped and as the printed cold pack is acted upon by the external pressure force, the application of the external pressure force to the printed cold pack thereby creating a pleasantly palpable sensation, the printed cold pack thereby providing cooling, supporting, and advertising means.

In another embodiment, I have provided a multifunctional cold pack comprising: a plurality of nonpermeable, flexible heat-sealable film layers each having a perimeter and being located in a first plane, the plurality of nonpermeable, flexible heat-sealable film layers being heat sealed together at the perimeters to form an interior cavity concentrically enclosed thereby, the interior cavity being geometrically contoured to coexist between the first plane and a second plane located parallel to the first plane, the plurality of nonpermeable, flexible heat-sealable film layers being constructed of a transparent material; a clear gelatinous material being encapsulated without air contamination within the interior cavity and having temperature regulation, flexibility, and load-bearing properties; and at least one insert being moldably movable and semi-rigidly placed in the clear gelatinous material and being sized, shaped, and dimensioned to be interposed between the plurality of nonpermeable, flexible heat-sealable film layers, the multifunctional cold pack thereby allowing each insert to be viewed through the plurality of nonpermeable, flexible heat-sealable film layers and the clear gelatinous material and imparting optical effects when each insert is so viewed, the multifunctional cold pack having a pleasant tactual texture when applying external pressure force to touch the plurality of nonpermeable, flexible heat-sealable film layers or to flex the multifunctional cold pack, the multifunctional cold pack being elastic and aesthetically appealing and thereby providing means for cooling, medicinal, supporting, advertising, entertaining, and shipping.

I have also provided a method of making a printed cold pack for cooling, supporting, medicinal, advertising, entertaining, aesthetically appealing, and shipping purposes, the method comprising the steps of: laying a coiled first film layer onto a support device; forming the laid first film layer to create a cavity; partially filling the cavity of the formed first film layer with a gelatinous material; chilling the gelatinous material in the partially filled cavity; placing a printed insert in the partially filled cavity; chilling the gelatinous material supporting the placed printed insert in the partially filled cavity; completely filling the partially filled cavity with the gelatinous material to encapsulate the placed printed insert; chilling the gelatinous material encapsulating the placed printed insert in the completely filled cavity; laying a coiled second film layer over the completely filled cavity; sealing the laid second film layer to the laid first film layer to sealingly enclose the gelatinous material and placed printed insert to form a printed cold pack; moving the support device aside and conveying the formed printed cold pack; cutting the sealed second film layer and the sealed first film layer on the conveyed printed cold pack; and ejecting the cut printed cold pack to a packaging device and collecting the scrap film layer.

DESCRIPTION OF THE DRAWINGS

Other features of my invention will become more evident from a consideration of the following detailed description of my patent drawings, as follows.

DETAILED DESCRIPTION OF THE PREFERRED EMBODIMENT

Figure 1:
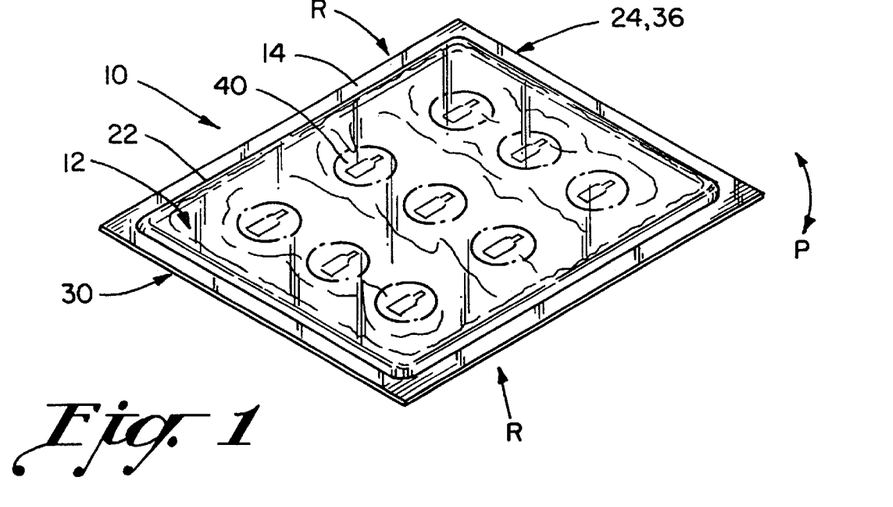
FIG. 1 is a perspective view of a first embodiment of my printed cold pack showing at least one printed insert and a first geometrical shape of a cavity and of each transparent film layer.
Figure 2:
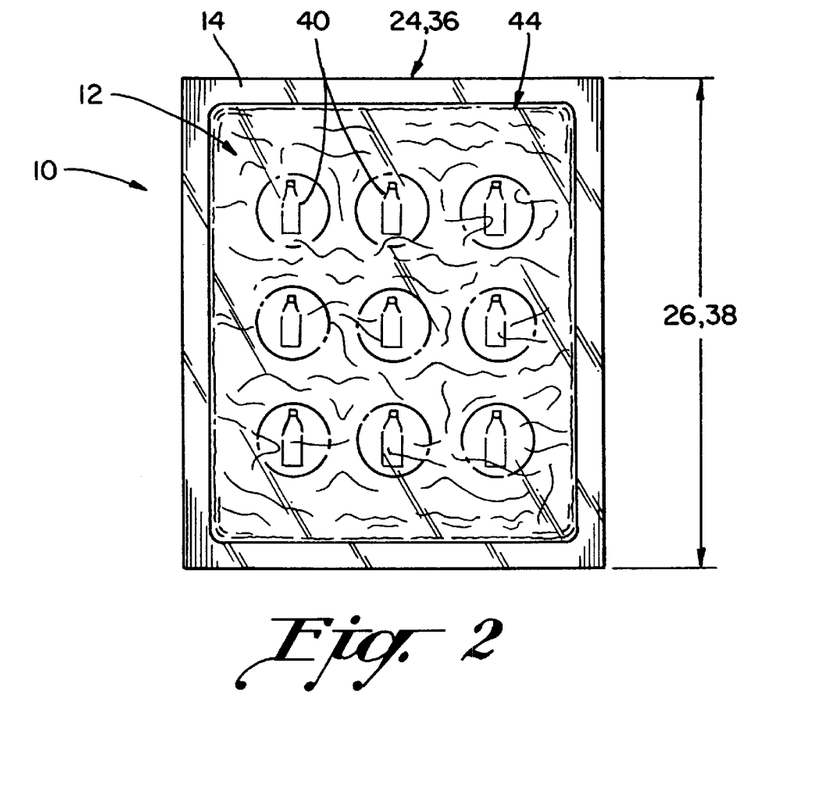
FIG. 2 is a top view of the first embodiment of FIG. 1.
Figure 3:
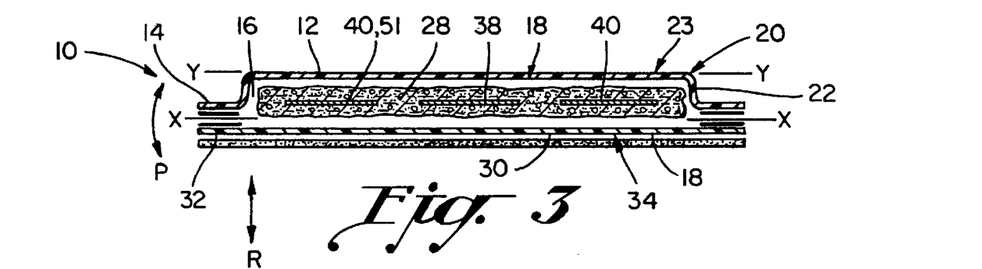
FIG. 3 is a sectional view of the first embodiment of FIG. 1 showing each transparent film layer, a clear gelatinous material, and at least one printed insert.
Figure 4:
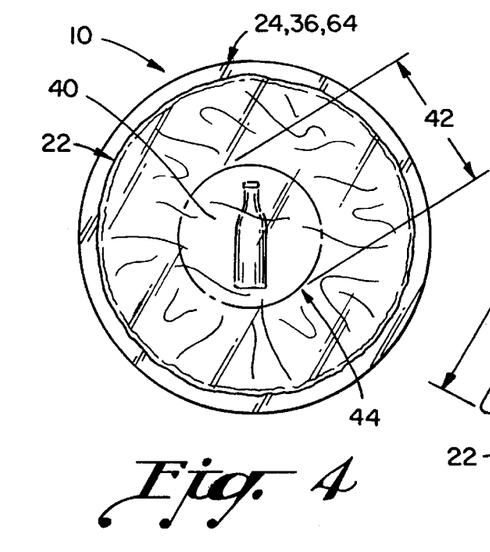
FIG. 4 is a top view of a second embodiment of my printed cold pack showing a second geometrical shape of the cavity and of each transparent film layer.

Referring now to the drawings, my invention is a printed cold pack 10 for advertising, cooling, medicinal, aesthetic, shipping, or entertainment purposes. This can also include such uses as in the food and medical industries. As shown in FIGS. 1–3, the printed cold pack 10, or multifunctional cold pack in other embodiments, comprises: a transparent formed film layer 12, a clear gelatinous material 28, a transparent nonformed film layer 30, and at least one printed insert 40. In other embodiments, the transparent formed film layer 12 and the transparent nonformed film layer 30 are a plurality of nonpermeable, flexible heat-sealable film layers and the printed insert 38 is an insert. My device also provides a sterile, lightweight cold pack.

As shown in FIGS. 1–3, the transparent formed film layer 30 has a first perimeter edge 14 and is capable of flexing, arrow P. The transparent formed film layer forms a cavity 16 and the transparent formed film layer is constructed of a nonpermeable, formable heat-sealable material, such as oriented nylon with an EVOH Barrier. In other embodiments, the transparent formed film layer can be constructed of a semi-rigid PVC material, any material common in the food industry, or of any other material that will exhibit properties of flexibility, nonpermeability, heat-sealability, and transparency or the ability to see through the film layer via a transparent material.

The first perimeter edge 14 is located in a first plane, X—X, and concentrically encloses the cavity 16. The cavity, or interior cavity in other embodiments, has a contour 20, and a geometrical edge 22 and is shaped in a second plane Y—Y. The contour can be geometrically contoured as will be explained below. The second plane is positioned in parallel, offset, and superimposed relation to the first plane, as shown in FIG. 3. The transparent formed film layer 12 has a tactual formed film layer texture 23, a formed film layer shape 24, and a formed film layer size 26.

Also shown in FIGS. 1–3 is the clear gelatinous material 28 which is placed within and substantially fills the cavity 16 so that the clear gelatinous material is free flowing and capable of moldable movement when pressed by the user. The clear gelatinous material is also encapsulated between the transparent formed film layer 12 and the transparent nonformed film layer 30 so as to be without substantial air contamination or substantially free of such bacteria-causing substances. This process will be further explained below.

Furthermore, the clear gelatinous material 28 has temperature retaining, temperature regulating, and load-bearing properties meaning that the material is capable of supporting a load, such as that of a beverage (not shown). The clear gelatinous material 28 is also capable of flexing, arrow P, and of elastically responding to an external pressure force, arrow R. In this way the printed cold pack 10 can be applied to an area to cool the area, such as in shipping uses, or the printed cold pack can be flexed and physically handled so as to provide a means for entertainment.

In order to perform as explained above and in the preferred embodiment, the clear gelatinous material 28 can contain from about 2 to 10 weight percent of bleach, about 2 to 10 weight percent of polyglycol, about 13 to 17 weight percent of methyl cellulose, about 3 to 7 weight percent of fungicide, and about 56 to 80 weight percent of water. In the preferred embodiment, the clear gelatinous material contains 10 weight percent of bleach, 10 weight percent of polyglycol, 15 weight percent of methyl cellulose, 5 weight percent of fungicide, and 60 weight percent of water to thereby provide the cooling and supporting means. All percentages being based upon percentage of sterile water weight. To vary the freezing time of the gel it is contemplated that the chemical composition can be altered as well as the number of printed cold packs used in a face-to-face relationship. The fungicide is a denatured alcohol.

The chemical composition of the gelatinous material is not intended to be limited to the concentrations and chemicals described above. It is contemplated that any other liquid, gel, gas, or solid that performs the stated functions and exhibits the stated features of my printed cold pack will be included in this description. One further point is the ability of my printed cold pack 10 and the gelatinous material to be capable of retaining heat.

Also as shown in FIGS. 1–3, the transparent nonformed film layer 30 has a second perimeter edge 32 that is sealingly connected to the first perimeter edge 14 to thereby sealingly enclose the clear gelatinous material 28 without the air contamination. In the preferred embodiment, the second perimeter edge is sealingly connected to the first perimeter edge by an ionomer, such as a surlyn-based adhesive.

The transparent nonformed film layer 30 is capable of flexing, arrow P, and is constructed of the nonpermeable, formable heat-sealable material 18. In the preferred embodiment, the transparent nonformed film layer is constructed of oriented nylon with an EVOH Barrier. In other embodiments, the transparent formed film layer can be constructed of a semi-rigid PVC material or of any other material that will exhibit the properties of flexibility, nonpermeability, heat-sealability, and see-throughability.

The second perimeter edge 32 is located in the first plane, X—X, and is substantially parallel to the first perimeter edge 14, as shown in FIG. 3. The transparent nonformed film layer 30 also has a tactual nonformed film layer texture 34, a nonformed film layer shape 36, and a nonformed film layer size 38. A further feature of my invention is the ability of the first perimeter edge and the second perimeter edge to be capable of receiving imprints for identification purposes (not shown). This could include both hot and cold stamp imprints, inking, and so forth.

A critical feature of my invention is the clarity of the transparent formed film layer 12, the transparent nonformed film layer 30, and the clear gelatinous material 28. This critical feature allows the printed insert(s) 40 to be viewed while being located in the gelatinous material. This will now be explained.

Figure 5:
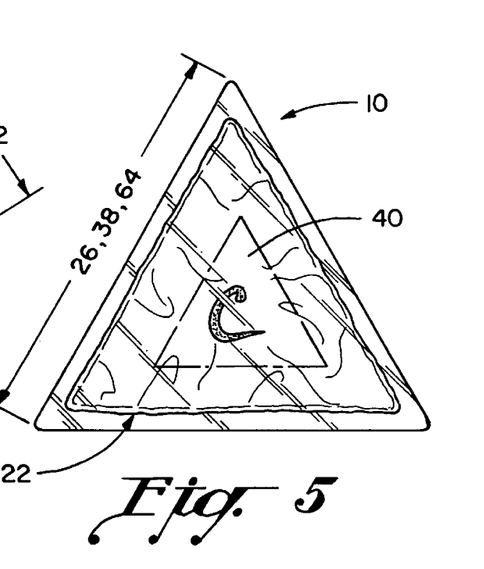
FIG. 5 is a top view of a third embodiment of my printed cold pack showing a third geometrical shape of the cavity and of each transparent film layer.
Figure 6:
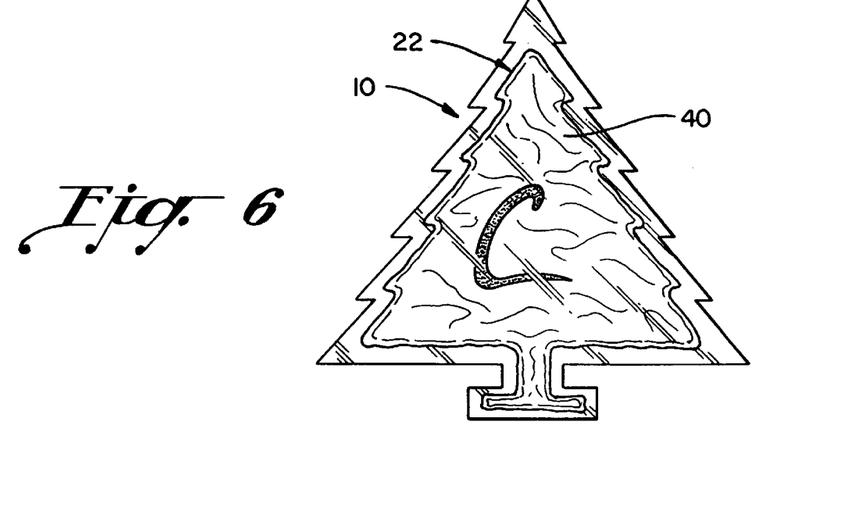
FIG. 6 is a top view of a fourth embodiment of my printed cold pack showing a fourth geometrical shape of the cavity and of each transparent film layer.
Figure 7:
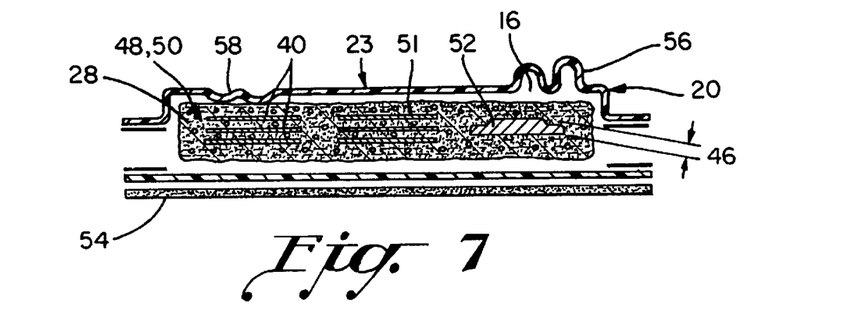
FIG. 7 is a sectional view of my printed cold pack showing at least two inserts being stacked in superimposed relation and a three dimensional object, the cavity having a convex shape and a concave shape, a laminate foam being adhesively connected to a transparent nonformed film layer.

At least one printed insert 40 having an insert size 42, an insert shape 44, and an insert dimension 46, shown in FIG. 7, is incrementally encapsulated and sandwiched within the clear gelatinous material 28. The printed insert can be semi-rigidly placed in the gelatinous material as will be explained below. In addition, each printed insert is sized and configured, or sized, shaped, and dimensioned, to be interposed between the transparent formed film layer 12 and the transparent nonformed film layer 30 and is oriented in the clear gelatinous material so as to be externally viewed (see FIGS. 1, 2, 4–6, 8 and 10) through either the transparent formed film layer or the transparent nonformed film layer and to impart optically aesthetic images 46, or optical effects, when so viewed. For example, as shown in FIGS. 1, 2, 4, and 8 an insignia of a bottle is externally viewed and in FIGS. 5, 6, and 10 a letter design is externally viewed. The type of insert and the designs are not intended to be limited to those shown in the figures.

In addition, the clear gelatinous material 28 is shaped readily by the external pressure force, arrow R and the printed insert 40 is capable of induced moldable movement, arrow T as shown in FIGS. 2–3, as the clear gelatinous material is shaped and as the printed cold pack is acted upon by the external pressure force, as by the touch of the user. The application of the external pressure force, arrow R, to the printed cold pack 10 thereby creates a pleasantly palpable sensation. This sensation is a key to the advertising use of the printed cold pack because the user has the desire to pick up the printed cold pack and to physically handle the printed cold pack while viewing the printed insert or advertisement inside. In addition, a game, such as a ball and maze or a basketball game, can be inserted into the clear gelatinous material 28, so that the user can physically handle and moldably move the insert for entertainment purposes.

The printed cold pack 10 thereby provides cooling, supporting, and advertising means. It is the ability to both see the printed insert 40 and to feel the texture, or tactual texture, of the film layers and the gelatinous material while holding, touching, and flexing the cold pack that are crucial to the printed cold pack's 10 use in advertising and entertaining the user or owner and these properties enhance the pack's aesthetic appeal. My invention can also act as a therapeutic mind-distracting device and may be disposable and/or reusable and it may used for medicinal purposes.

Figure 8:
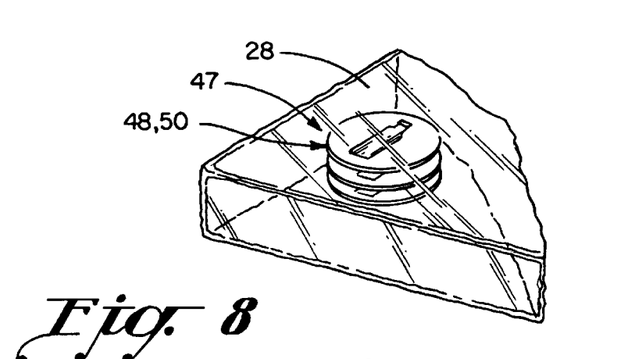
FIG. 8 is a fragmentary perspective view of the clear gelatinous material in the cavity in FIG. 7 showing at least two printed inserts stacked in superimposed relation.

Another critical feature of my invention is the versatility of the placement of the inserts 40 that can be placed or encapsulated within the clear gelatinous material 28. In one embodiment, as shown in FIG. 7, at least two printed inserts 40 are stacked in superimposed relation 48 to one another to form at least one three dimensional image 50, as shown in FIG. 8. This stacking relationship thereby modifies the insert dimension 46 and enhances the view of the optically aesthetic images 47 as well as the advertising means of the printed cold pack 10. The insert dimension can be either two dimensional or three dimensional, as shown in FIG. 7, by means of the type of insert placed within the clear gelatinous material 28 as will be explained below. Furthermore, each insert is not to be limited to parallel placement in the gelatinous material with respect to one another or to the surrounding layers. In addition, the printed inserts are capable of being stacked in staggered superimposed relation (not shown) to one another by placing the inserts at different levels in the gelatinous material as the gelatinous material is added to the cavity 16 and the inserts can be mixed and matched. This process will also be explained below.

Another critical feature of my invention is the versatility of the types of inserts 40 that can be placed or encapsulated within the clear gelatinous material 28 and the corresponding optical effect 47 imparted by each type of insert. In one embodiment, as shown in FIGS. 3, 7–9, a printed insert can be constructed of nonpermeable vinyl or polyacetate material, such as a sheet of film whereupon are printed images, letters, numbers, designs, and so forth. In addition, at least one printed insert can be positioned to form at least one two dimensional image 51, as shown in FIG. 3. In another embodiment, as shown in FIG. 7, at least one printed insert can be a three dimensional object 52. In still another embodiment, at least one printed insert can be a holographic image (not shown) and the holographic image thereby modifies the insert dimension 46 and enhances the view of the optically aesthetic images 47 and the advertising means of the printed cold pack 10 as the printed cold pack is viewed in motion or as it is turned from side-to-side. In other embodiments, each insert can have at least one two or greater dimensioned printed or design characteristic or a design image.

A further feature and advantage of my invention is that the printed cold pack 10 can further comprise a laminate foam 54, shown in FIG. 7, that is adhesively connected to the transparent nonformed film layer 30 to form an absorbent, support structure for beverages and food products. In this way, the printed cold pack 10 can act as a coaster. The load-bearing properties of the clear gelatinous material 28 thereby act to support the beverage or food product.

Figure 9:
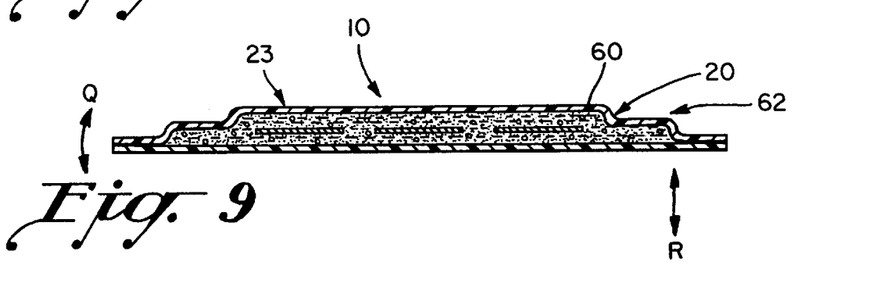
FIG. 9 is a sectional view of a fifth embodiment of my printed cold pack showing the cavity having a geometrical shape.
Figure 10:
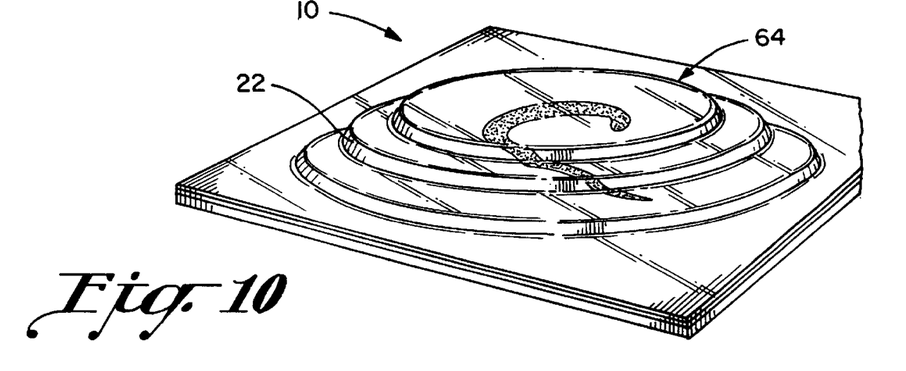
FIG. 10 is a fragmentary perspective view of the fifth embodiment of FIG. 9.

In another feature of my printed cold pack 10, as shown in FIG. 7 and 9, the contour 20 of the cavity 16 can have a convex shape 56, a concave shape 58, a geometrical shape 60, or a combination of shapes, such as shown in FIG. 7. The contour is capable of a three dimensional appearance 62, as shown in FIGS. 9 and 10, and the formed film layer shape 24 and the nonformed film layer shape 36 each have a geometrical film layer shape 64 with the geometrical edge 22 of the contour being shaped to conform to the geometrical film layer shape, as shown in FIGS. 2, 4–6. In other embodiments, the geometrically contoured interior cavity has a geometrical cavity shape that is slightly smaller and similar to the geometrical shapes of the plurality of nonpermeable, flexible heat-sealable film layers. For example, as shown in FIG. 6, the geometrical cavity shape has a christmas tree shape as does the geometrical shapes of the plurality of nonpermeable, flexible heat-sealable film layers.

As shown in these figures the geometrical shape can be as simple as a rectangle, a triangle, and a circle and as complex as a christmas tree shape. These shapes are not intended to be limited to the geometrical shapes shown.

Furthermore, the insert size 42 and the insert shape 44 are sized and geometrically shaped to substantially conform and interpose between the transparent formed film layer 12 and the transparent nonformed film layer 30. These sizes are intended to vary depending upon the use for which the printed cold pack 10 is created and the insert 40 can be sized and shaped in any way the fits within the cavity 16. The contour 20, the geometrical film layer shape 64, the insert size, and the insert shape each enhance the view of the optically aesthetic images 47 and the advertising means of the printed cold pack and enhance the pleasantly palpable sensation.

A further feature and advantage of my invention is that the formed film layer shape 24 and the nonformed film layer shape 36 have substantially similar geometrical film layer shapes, as shown in FIGS. 1, 2, 4–6, and 10 and the formed film layer size 26 and the nonformed film layer size 38 have similar sizes for ease of connection of the transparent formed film layer 12 to the transparent nonformed film layer 30. In this way the first perimeter edge 14 and the second perimeter edge 32 can be heat-sealed together by a process described below.

Finally, the transparent formed film layer 12 and the transparent nonformed film layer 30 are also each capable of receiving design images (not shown) and the transparent formed film layer, the transparent nonformed film layer, the clear gelatinous material 28, and at least one printed insert 40 are modifiable individually or in combination to a colored appearance (not shown), such as green for the christmas tree shown in FIG. 6, while still retaining the capability of externally viewing the printed insert. In this way the view of the optically aesthetic images 46 and the advertising means of the printed cold pack are thereby enhanced and in the above stated description are the overall objects of my invention are met.

Figure 11:
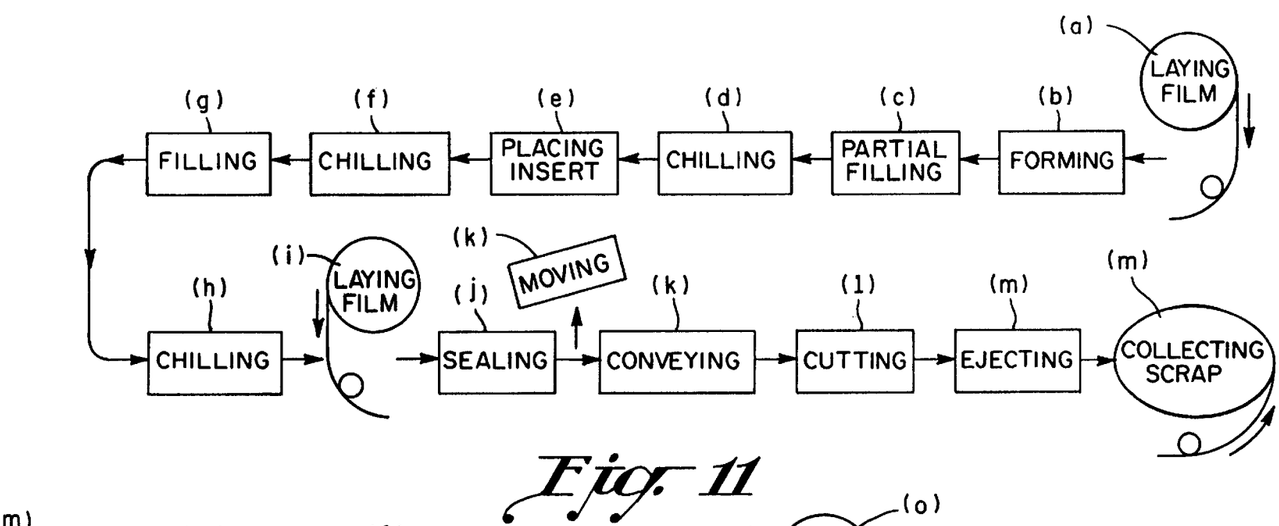
FIG. 11 is a diagramatic view of a method of making my printed cold pack.

I also disclose a method of making my invention, the printed cold pack 10, for cooling, supporting, advertising, entertaining, aesthetically appealing, and shipping purposes. As shown in FIG. 11, the method comprises the steps (marked by the letters) of: (a) laying a coiled first film layer onto a support device; (b) forming the laid first film layer to create a cavity; (c) partially filling the cavity of the formed first film layer with a gelatinous material; (d) chilling the gelatinous material in the partially filled cavity; (e) placing a printed insert in the partially filled cavity; (f) chilling the gelatinous material supporting the placed printed insert in the partially filled cavity; (g) completely filling the partially filled cavity with the gelatinous material to encapsulate the placed printed insert; (h) chilling the gelatinous material encapsulating the placed printed insert in the completely filled cavity; (i) laying a coiled second film layer over the completely filled cavity; (j) sealing the laid second film layer to the laid first film layer to sealingly enclose the gelatinous material and placed printed insert to form a printed cold pack; (k) moving the support device aside and conveying the formed printed cold pack; (l) cutting the sealed second film layer and the sealed first film layer on the conveyed printed cold pack; and (m) ejecting the cut printed cold pack to a packaging device and collecting the scrap film layer.

As to the steps of chilling, the chilling is performed to quickly chill the gelatinous material 28 within the cavity 16 to dissipate the heat from the liquified gel as it is originally placed in the cavity. The process of chilling also acts to speed up the manufacturing process of making the printed cold packs 10. In addition, the quickly chilled nature of the gelatinous material aids in preventing the gelatinous material from spilling out of the cavity during the manufacturing process.

As to the sealing stage, a vacuum seal is used to evacuate substantial air out of the cavity/gelatinous material medium so as to provide a sterile environment within the sealed cavity. A nitrogen gas flush may also be used to displace oxygen. In addition, each succeeding layer in the manufacturing process, meaning the formed layer, the gelatinous material/printed insert, and the nonformed layer, and so forth can each have a slightly larger sized perimeter so that during the sealing and vacuum process air is easier to draw out of the gelatinous material/cavity medium. In addition, during the cutting stage a hot die cutter is the preferred manner of cutting, though other cutting means, such as a cold cutting means, can be used for creating a smooth, sealed edge around the printed cold pack 10.

Figure 12:
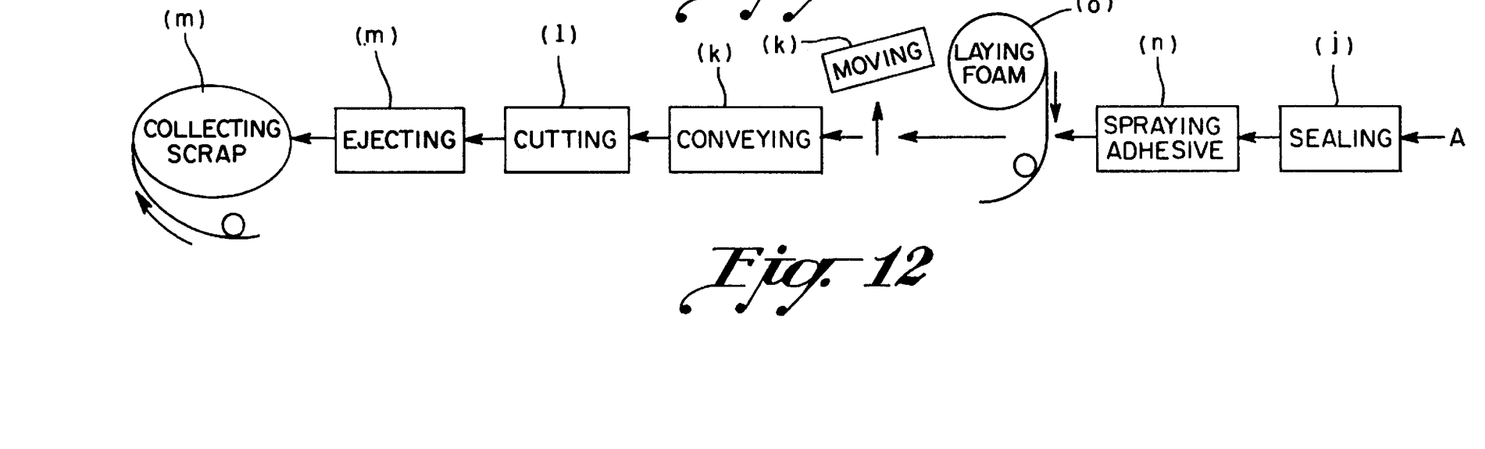
FIG. 12 is a diagramatic view of the method of making my printed cold pack in FIG. 11 further comprising the steps added at the point "A".

As shown in FIG. 12, the method of making the printed cold pack 10 further comprises the steps starting with point "A" of FIG. 11 (the steps being shown by numbers) of: (n) spraying an adhesive on the sealed second layer and (o) laying a coiled foam laminate layer 54 onto the sprayed, sealed second layer, or the transparent nonformed film layer 30, to create a foam laminated printed cold pack prior to moving the support device and conveying the foam laminated printed cold pack towards cutting.

Further modifying steps in the method of making the printed cold pack 10 include partially filling the cavity 16 of the formed first film layer 12 with a gelatinous material 28, chilling the gelatinous material in the partially filled cavity, placing a printed insert 40 in the partially filled cavity, and chilling the gelatinous material supporting the placed printed insert in the partially filled cavity. These steps are to be sequentially repeated so that the printed inserts thereby superimposing each successively placed printed insert above the previous placed printed insert and thereby creating a three dimensional image, as shown in FIG. 8, prior to completely filling the partially filled cavity with the gelatinous material to encapsulate the placed printed inserts.

The method of making the printed cold pack 10 can also further comprise the successive steps of partially filling a first portion 80, as shown in FIG. 7, of the cavity 16 of the formed first film layer with a gelatinous material 28; chilling the gelatinous material in the partially filled first portion of the cavity; placing a printed insert 40 in the partially filled first portion of the cavity; chilling the gelatinous material supporting the placed printed insert in the partially filled first portion of the cavity; partially filling a second portion 82, as shown in FIG. 7, of the cavity of the formed first film layer with a gelatinous material; chilling the gelatinous material in the partially filled second portion of the cavity; placing a printed insert 41 in the partially filled second portion of the cavity; chilling the gelatinous material supporting the placed printed insert in the partially filled second portion of the cavity; and repeating these successive steps prior to completely filling the partially filled cavity with the gelatinous material to thereby create a staggered superimposed (not shown) three dimensional image of the printed inserts. Also shown in FIG. 7, the step of placing further comprises placing at least one three dimensional object 52 in the partially filled cavity 16. Finally, the step of forming the laid first film layer further includes forming a geometrically shaped and geometrically dimensioned cavity 16 and the step of cutting the sealed second film layer and the sealed first film layer on the conveyed printed cold pack further includes creating a geometrically shaped cut printed cold pack, such as those shown in FIGS. 2, 4–6. The step of cutting is capable of being performed on the support device prior to conveying the cut printed cold pack.

As various possible embodiments may be made in the above invention for use for different purposes and as various changes might be made in the embodiments and methods above set forth, it is understood that all of the above matters here set forth or shown in the accompanying drawings are to be interpreted as illustrative and not in a limiting sense.

I claim:

1. A printed cold pack for advertising, cooling, medicinal, aesthetic, shipping, or entertainment purposes comprising:

a transparent formed film layer having a first perimeter edge, being capable of flexing, and forming a cavity, the transparent formed film layer being constructed of a nonpermeable, formable heat-sealable material, the first perimeter edge being located in a first plane and concentrically enclosing the cavity, the cavity having a contour and a geometrical edge, and being shaped in a second plane, the second plane being positioned in parallel, offset, and superimposed relation to the first plane, the transparent formed film layer having a tactual formed film layer texture, a formed film layer shape, and a formed film layer size;

a clear gelatinous material placed within and substantially filling the cavity, the clear gelatinous material being free flowing and having temperature retaining and load-bearing properties and being capable of flexing and elastically responding to an external pressure force;

a transparent nonformed film layer having a second perimeter edge being sealingly connected to the first perimeter edge to thereby sealingly enclose the clear gelatinous material without air contamination, the transparent nonformed film layer being capable of flexing, the transparent nonformed film layer being constructed of nonpermeable, formable heat-sealable material, the second perimeter edge being located in the first plane and being substantially parallel to the first perimeter edge, the transparent nonformed film layer having a tactual nonformed film layer texture, a nonformed film layer shape, and a nonformed film layer size; and at least one printed insert having an insert size, an insert shape, and an insert dimension, each printed insert being incrementally encapsulated and sandwiched within the clear gelatinous material and being sized and configured to be interposed between the transparent formed film layer and the transparent nonformed film layer, the printed insert being oriented in the clear gelatinous material so as to be externally viewed through either the transparent formed film layer or the transparent nonformed film layer and to impart optically aesthetic images when so viewed, the clear gelatinous material being shaped readily by the external pressure force, the printed insert being capable of induced moldable movement as the clear gelatinous material is shaped and as the printed cold pack is acted upon by the external pressure force, the application of the external pressure force to the printed cold pack thereby creating a pleasantly palpable sensation, the printed cold pack thereby providing cooling, supporting, and advertising means.

2. The printed cold pack of claim 1, wherein the clear gelatinous material contains from about 2 to 10 weight percent of bleach, about 2 to 10 weight percent of polyglycol, about 13 to 17 weight percent of methyl cellulose, about 3 to 7 weight percent of fungicide, and about 56 to 80 weight percent of water, the transparent formed film layer and the transparent nonformed film layer being constructed of oriented nylon with an EVOH Barrier, and the second perimeter edge being sealingly connected to the first perimeter edge by an ionomer, such as a surlyn-based adhesive.

3. The printed cold pack of claim 2, wherein the clear gelatinous material contains 10 weight percent of bleach, 10 weight percent of polyglycol, 15 weight percent of methyl cellulose, 5 weight percent of fungicide, and 60 weight percent of water to thereby provide the cooling and supporting means, the fungicide being denatured alcohol.

4. The printed cold pack of claim 3, wherein at least two printed inserts are stacked in superimposed relation to one another to form at least one three dimensional image to thereby modify the insert dimension and to enhance the view of the optically aesthetic images and the advertising means of the printed cold pack, the insert dimension being two dimensional or three dimensional, the printed inserts being capable of being stacked in staggered superimposed relation to one another.

5. The printed cold pack of claim 4, wherein each printed insert is constructed of nonpermeable vinyl or polyacetate material.

6. The printed cold pack of claim 4, wherein at least one printed insert is a three dimensional object.

7. The printed cold pack of claim 4, wherein at least one printed insert is positioned to form at least one two dimensional image.

8. The printed cold pack of claim 4, wherein at least one printed insert is a holographic image to thereby modify the insert dimension and to enhance the view of the optically aesthetic images and the advertising means of the printed cold pack as the printed cold pack is viewed in motion.

9. The printed cold pack of claim 4, further comprising a laminate foam being adhesively connected to the transparent nonformed film layer to form an absorbent, support structure for beverages and food products.

10. The printed cold pack of claim 4, wherein the contour of the cavity has a convex shape, a concave shape, a geometrical shape, or a combination of shapes, the contour being capable of a three dimensional appearance, the formed film layer shape and the nonformed film layer shape each having a geometrical film layer shape, the geometrical edge of the contour being shaped to conform to the geometrical film layer shape, the insert size and the insert shape being sized and geometrically shaped to substantially conform and interpose between the transparent formed film layer and the transparent nonformed film layer, the contour, the geometrical film layer shape, the insert size, and the insert shape each thereby enhancing the view of the optically aesthetic images and the advertising means of the printed cold pack and enhancing the pleasantly palpable sensation.

11. The printed cold pack of claim 10, wherein the formed film layer shape and the nonformed film layer shape have substantially similar geometrical film layer shapes and the formed film layer size and the nonformed film layer size have similar sizes for ease of connection of the transparent formed film layer to the transparent nonformed film layer, the transparent formed film layer and the transparent nonformed film layer each being capable of receiving design images and the transparent formed film layer, the transparent nonformed film layer, the clear gelatinous material, and at least one printed insert being modifiable individually or in combination to a colored appearance while retaining the capability of externally viewing the printed insert to thereby enhance the view of the optically aesthetic images and the advertising means of the printed cold pack.

12. The printed cold pack of claim 4, wherein the nonpermeable, formable heat-sealable material is a semi-rigid PVC material, the first perimeter edge and the second perimeter edge being capable of receiving imprints for identification purposes, the printed cold pack being capable of retaining heat.

13. A multifunctional cold pack comprising:
  a plurality of nonpermeable, flexible heat-sealable film layers each having a perimeter and being located in a first plane, the plurality of nonpermeable, flexible heat-sealable film layers being heat sealed together at the perimeters to form an interior cavity concentrically enclosed thereby, the interior cavity being geometrically contoured to coexist between the first plane and a second plane located parallel to the first plane, the plurality of nonpermeable, flexible heat-sealable film layers being constructed of a transparent material;
  a clear gelatinous material being encapsulated without substantial air contamination within the interior cavity and having temperature regulation, flexibility, and load-bearing properties; and
  at least one insert being moldably movable and semi-rigidly placed in the clear gelatinous material and being sized, shaped, and dimensioned to be interposed between the plurality of nonpermeable, flexible heat-sealable film layers, the multifunctional cold pack thereby allowing each insert to be viewed through the plurality of nonpermeable, flexible heat-sealable film layers and the clear gelatinous material and imparting optical effects when each insert is so viewed, the multifunctional cold pack having a pleasant tactual texture when applying external pressure force to touch the plurality of nonpermeable, flexible heat-sealable film layers or to flex the multifunctional cold pack, the multifunctional cold pack being elastic and aesthetically appealing and thereby providing means for cooling, supporting, medicinal, advertising, entertaining, and shipping.

14. The multifunctional cold pack of claim 13, wherein the clear gelatinous material contains from about 2 to 10 weight percent of bleach, about 2 to 10 weight percent of polyglycol, about 13 to 17 weight percent of methyl cellulose, about 3 to 7 weight percent of fungicide, and about 56 to 80 weight percent of water, the plurality of nonpermeable, flexible heat-sealable film layers being constructed of oriented nylon with an EVOH Barrier, and the perimeters being sealingly connected to one another by an ionomer, such as a surlyn-based adhesive.

15. The multifunctional cold pack of claim 14, wherein the geometrically contoured interior cavity has a convex shape, a concave shape, a geometrical shape, or a combination of shapes to thereby enhancing the aesthetic appeal, palpability, and advertising means of the multifunctional cold pack, the geometrically contoured interior cavity being capable of a three dimensional appearance, the plurality of nonpermeable, flexible heat-sealable film layers each having substantially similar geometrical shapes and similar sizes for ease of heat-seal connection and for aesthetic purposes, the geometrically contoured interior cavity having a geometrical cavity shape slightly smaller and similar to the geometrical shapes of the plurality of nonpermeable, flexible heat-sealable film layers, each insert having at least one two or greater dimensioned printed or design characteristic being capable of imparting the optical effects to thereby enhance palpability, aesthetics, and advertising use of the multifunctional cold pack.

16. The multifunctional cold pack of claim 15, wherein at least two inserts are stacked in superimposed relation or staggered superimposed relation to one another to form at least one three dimensional image to thereby enhance the optical effects, aesthetic appeal, and advertising means of the multifunctional cold pack, each insert being two dimensional or three dimensional.

17. The multifunctional cold pack of claim 16, wherein the plurality of nonpermeable, flexible heat-sealable film layers are each capable of receiving design images and the plurality of nonpermeable, flexible heat-sealable film layers, the clear gelatinous material, and at least one insert are modifiable individually or in combination to a colored appearance while retaining the ability to view the insert, at least one insert being a three dimensional object or a holographic image to thereby enhance the visual properties, aesthetic appeal, and advertising means of the printed cold pack when the printed cold pack is viewed in motion.

18. The multifunctional cold pack of claim 17, wherein the clear gelatinous material contains from about 2 to 10 weight percent of bleach, about 2 to 10 weight percent of polyglycol, about 13 to 17 weight percent of methyl cellulose, about 3 to 7 weight percent of fungicide, and about 56 to 80 weight percent of water, each insert being constructed of nonpermeable vinyl or polyacetate material, and the plurality of nonpermeable, flexible heat-sealable film layers being heat sealed by the surlyn-based adhesive, a laminate foam being adhesively connected to one of the plurality of nonpermeable, flexible heat-sealable film layers to form an absorbent, support structure for beverages and food products.

19. The multifunctional cold pack of claim 13, wherein the plurality of nonpermeable, flexible heat-sealable film layers is constructed of a semi-rigid PVC material, each perimeter being capable of receiving imprints for identification purposes.

* * * * *